United States Patent [19]

Baier

[11] Patent Number: 5,882,930
[45] Date of Patent: Mar. 16, 1999

[54] REAGENT TRANSFER DEVICE

[75] Inventor: Joerg Baier, Foster City, Calif.

[73] Assignee: Hyseq, Inc., Sunnyvale, Calif.

[21] Appl. No.: 966,893

[22] Filed: Nov. 10, 1997

[51] Int. Cl.$^6$ .................................................. G01N 35/10
[52] U.S. Cl. ................................ 436/49; 436/43; 436/54;
436/180; 422/63; 422/81; 422/100; 422/102;
422/103; 73/864.23; 73/864.24; 73/864.02;
435/288.4
[58] Field of Search .................................. 422/63, 65, 67,
422/81, 100, 102, 103; 436/43, 47, 174,
54, 180, 807, 809; 73/864.02, 864.23, 864.24;
435/288.4

[56] References Cited

U.S. PATENT DOCUMENTS

| | | | |
|---|---|---|---|
| 3,568,735 | 3/1971 | Lancaster | 141/238 |
| 3,863,507 | 2/1975 | Jones et al. | 73/423 A |
| 4,106,911 | 8/1978 | Marcelli | 73/425.6 |
| 4,140,018 | 2/1979 | Maldarelli et al. | 73/423 A |
| 4,199,013 | 4/1980 | Reich et al. | 141/130 |
| 4,224,278 | 9/1980 | Esch | 422/65 |
| 4,276,048 | 6/1981 | Leaback | 422/100 |
| 4,334,879 | 6/1982 | Fujimori | 422/99 |
| 4,422,151 | 12/1983 | Gilson | 364/496 |
| 4,459,265 | 7/1984 | Berglund | 422/64 |
| 4,483,925 | 11/1984 | Noack | 435/293 |
| 4,621,665 | 11/1986 | Webb | 141/1 |
| 4,699,884 | 10/1987 | Noss et al. | 435/287 |
| 4,731,335 | 3/1988 | Brigati | 436/180 |
| 5,000,921 | 3/1991 | Hanaway et al. | 422/100 |
| 5,008,082 | 4/1991 | Shaw | 422/65 |
| 5,055,263 | 10/1991 | Meltzer | 422/65 |
| 5,166,889 | 11/1992 | Cloyd | 364/510 |
| 5,188,148 | 2/1993 | Garrison | 137/606 |
| 5,262,128 | 11/1993 | Leighton et al. | 422/100 |
| 5,334,352 | 8/1994 | Johnson | 422/99 |
| 5,338,688 | 8/1994 | Deeg et al. | 436/180 |
| 5,551,487 | 9/1996 | Gordon et al. | 141/1 |
| 5,736,105 | 4/1998 | Astle | 422/100 |
| 5,756,050 | 5/1998 | Ershow et al. | 422/100 |
| 5,770,151 | 6/1998 | Roach et al. | 422/63 |
| 5,772,966 | 6/1998 | Maracas et al. | 422/100 |

OTHER PUBLICATIONS

John R. Harvey, U.S. Patent and Trademark Office Patent Database Search Results, Oct. 7, 1997, pp. 2–15.

*Primary Examiner*—Long V. Le
*Attorney, Agent, or Firm*—Marshall, O'Toole, Gerstein, Murray & Borun

[57] ABSTRACT

The present device is directed to a reagent transfer device for transferring a plurality of reagent samples from one location to another location having a deposit surface. The device includes a reagent tray having a top surface with a top surface area and a plurality of wells in the ratio of at least 1,000 wells per square centimeter of top surface area, and a transfer member having a transfer surface with a plurality of pins extending therefrom. Each of the pins is positioned to correspond to one of the wells so that when the transfer member is moved in the Z-direction the pins are simultaneously dipped into the corresponding wells. The device further includes a mechanism for moving the transfer member between a first position in which reagent from the wells is deposited onto the corresponding pins and a second position in which reagent on the pins is deposited on the deposit surface. The mechanism for moving is adapted to move the transfer member in the X-direction, the Y-direction and the Z-direction.

5 Claims, 3 Drawing Sheets

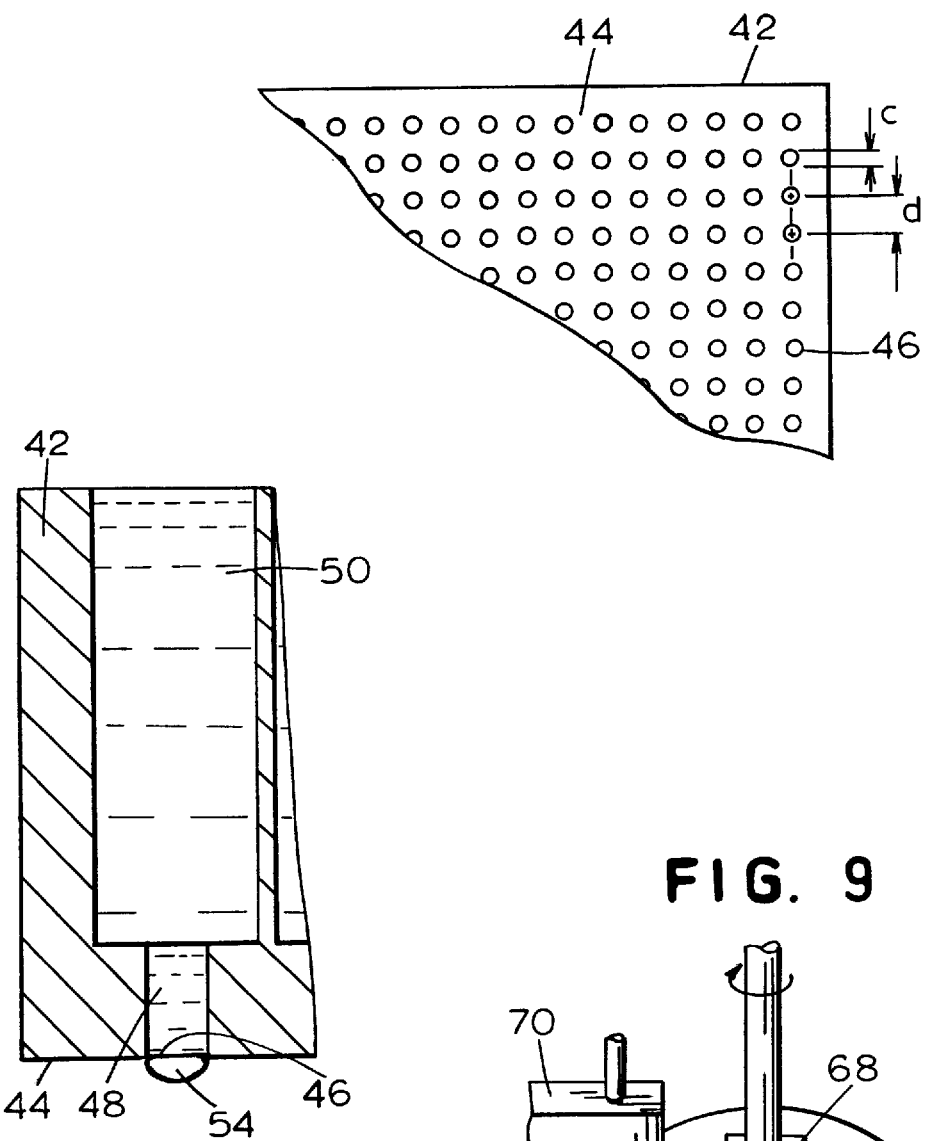
FIG. 7
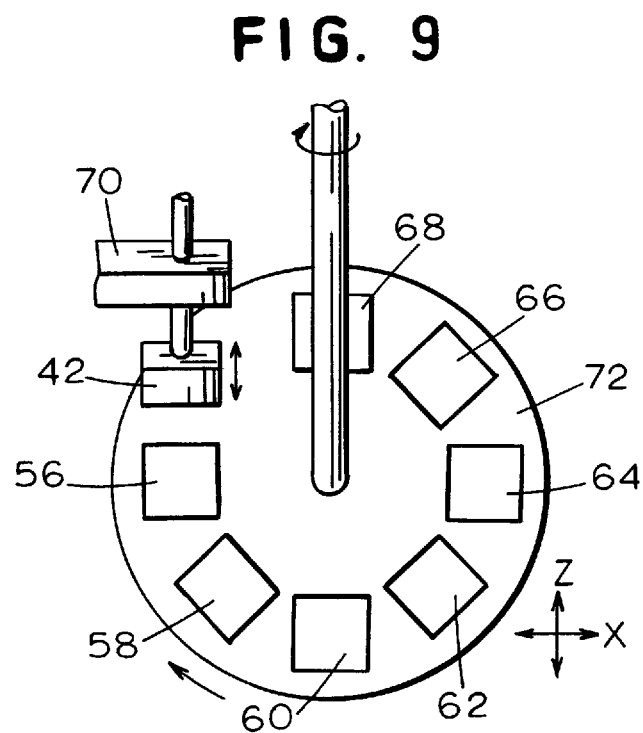
FIG. 8
FIG. 9

REAGENT TRANSFER DEVICE

BACKGROUND OF THE INVENTION

1. Field of the Invention

The present invention relates to transferring fluid samples and, more particularly, to a reagent transfer device for transferring a large number of fluid samples onto a very small surface area.

2. Description of the Related Art

Automated systems are used to transfer fluid samples from repositories, such as test tubes, vials or wells, to receptacles or surfaces. One such automated system is disclosed in U.S. Pat. No. 5,055,263, issued to Meltzer, entitled "Automated Pipetting System." This reference discloses a system wherein a plurality of hollow probes are used to transfer a plurality of fluid samples. A probe is dipped into the fluid repository and a volume of fluid is drawn into the probe using aspiration. The probe is retracted from the repository and repositioned above the receptacle or surface that will receive the fluid sample. The probe is lowered towards the surface and pressure is exerted against the fluid to force the fluid sample out of the probe. A plurality of probes are mounted on a carriage that is in turn mounted to an overhead frame assembly which moves the carriage independently in the X-direction and Y-direction. The carriage includes a drive mechanism that moves each probe independently in the Z-direction.

The system described above is effective for transferring fluid samples from test tubes and vials. However, the use of hollow probes to transfer fluid samples from a plurality of repositories does not provide the precision necessary to transfer a plurality of fluid samples that are in the range of about 100 microns in diameter and spaced apart by a distance of less than about 500 microns.

SUMMARY OF THE INVENTION

The present invention is directed to a reagent transfer device for transferring a plurality of reagent samples onto a deposit surface. In one embodiment of the present invention, the reagent transfer device includes a reagent tray having a top surface with a top surface area and a plurality of wells arranged in a two-dimensional array of at least 30 wells by at least 30 wells. The wells have a diameter of no greater than about 300 microns and are spaced apart by a center-to-center distance measured from the center of one well to the center of an adjacent well of less than about 500 microns. The reagent tray may further include a bottom surface having a bottom surface area larger than the top surface area, a plurality of coupling cavities, and a plurality of channels. Each of the channels connects one of the wells to a corresponding one of the coupling cavities so that the one well and the one corresponding coupling cavity are in fluid communication so as to allow replenishment of the one well by providing reagent to the one well through the one corresponding coupling cavity and the channel.

The reagent transfer device further includes a transfer member having a transfer surface with a two-dimensional array of pins extending therefrom. Each of the pins is positioned to correspond to one of the wells so that when the transfer member is moved in the Z-direction the pins are simultaneously dipped into the corresponding wells. The reagent transfer device also includes a means for moving the transfer member between a first position in which reagent from the wells is deposited on the pins and a second position in which reagent on the pins is deposited on the deposit surface. The moving means may be adapted for independent movement of the transfer member in the X-direction, the Y-direction, and the Z-direction. Alternatively, the moving means may be adapted to move the transfer member in the Z-direction, and to move the deposit surface in the X-direction and the Y-direction.

According to one aspect of the present invention, each of the pins has a diameter in the range of between about 30 microns and about 100 microns, and has an outer shape adapted to retain a sample of one of the reagents when the pin is dipped into the corresponding one of the wells. In another aspect of the present invention, at least about 100 wells are disposed on the top surface of the reagent tray in the ratio of at least 100 wells per square centimeter of top surface area.

In another aspect of the present invention, a method for transferring a plurality of reagent samples from a reagent tray via a transfer member to a deposit surface is provided. The reagent tray has a top surface with a top surface area and at least about 100 wells in the ratio of at least 100 wells per square centimeter of top surface area. The transfer member has a transfer surface with a plurality of pins extending therefrom. Each of the pins is positioned to correspond to one of the wells so that when the transfer member is moved in the Z-direction, the pins are simultaneously dipped into the corresponding wells.

The method according to the present invention includes the steps of dipping the pins into the corresponding wells so that a reagent sample is deposited on each of the pins by adhesion to the outer surfaces of the pins, moving the transfer member to a position proximate the deposit surface, and contacting the deposit surface with the reagent samples, whereby the reagent samples are deposited on the deposit surface by adhesion to the deposit surface. In one aspect, the method according to the present invention further includes the step of replenishing the reagent in the wells by providing reagent to the wells through corresponding coupling cavities and channels in the reagent tray.

In another alternative embodiment of the present invention, the reagent transfer device includes a transfer member having a bottom surface with a bottom surface area and at least about 100 orifices in the ratio of at least 100 orifices per square centimeter of bottom surface area. The transfer member further includes a top surface having a plurality of reservoirs and a plurality of channels. Each of the channels connects one of the orifices to a corresponding one of the reservoirs so that the one orifice and the one corresponding reservoir are in fluid communication. A reagent sample is formed on the bottom surface about the orifice by providing reagent to the orifice through the corresponding one reservoir and the channel. The reagent transfer device further includes a means for moving the transfer member between a first position in which reagent samples are deposited onto a first deposit surface and a second position in which reagent samples are deposited on a second deposit surface. The means for moving the transfer member may be adapted to move the transfer member in the X-direction, the Y-direction and the Z-direction. Alternatively, the means for moving may be adapted to move the transfer member in the Z-direction, and to move the first and the second deposit surfaces in the X-direction and the Y-direction.

In yet another embodiment of the present invention, a method for depositing a plurality of reagent samples via a transfer member onto a deposit surface is provided. The transfer member includes a bottom surface with a bottom surface area and at least about 100 orifices in the ratio of at least 100 orifices per square centimeter of bottom surface area. The transfer member further includes a top surface having a plurality of reservoirs and a plurality of channels. Each of the channels connects one of the orifices to a corresponding one of the reservoirs so that the one orifice and the one corresponding reservoir are in fluid communication. The method includes the steps of forming a reagent sample on the bottom surface of the orifice by providing reagent to the orifice through the one corresponding reservoir and the channel, moving the transfer member to a position proximate the deposit surface, and contacting the deposit surface with the reagent samples whereby the reagent samples are deposited on the deposit surface by adhesion to the deposit surface.

The features and advantages of the invention will be apparent to those of ordinary skill in art in view of the detailed description of the preferred embodiment, which is made with reference to the drawings, a brief description of which is provided below.

BRIEF DESCRIPTION OF THE DRAWINGS

FIG. 7 is a partial bottom view of the transfer member of FIG. 6;

FIG. 8 is an enlarged partial sectional view of the transfer member of FIG. 6; and FIG. 9 is a schematic view of a system for transferring reagent samples from the transfer member of FIG. 6 to a plurality of deposit surfaces.

DETAILED DESCRIPTION OF THE PREFERRED EMBODIMENTS

Figure 1:
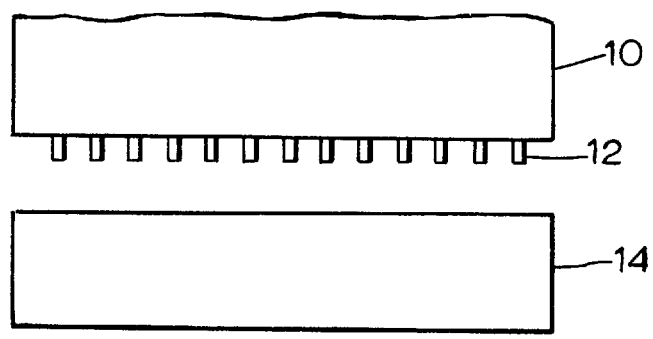
FIG. 1 is a partial side view of a transfer member and reagent tray in accordance with the present invention.
Figure 2:
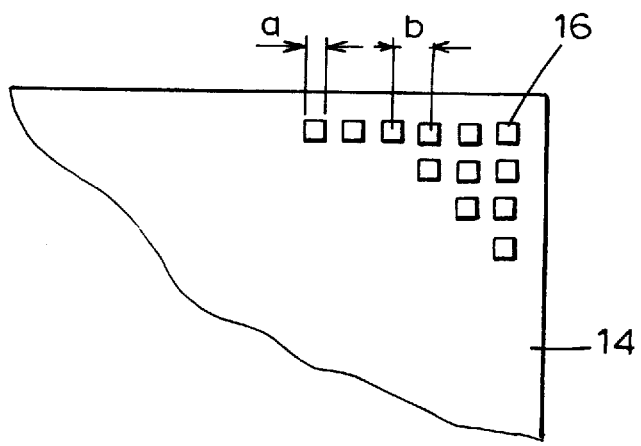
FIG. 2 is a partial top view of the reagent tray of FIG. 1.

The first embodiment of a reagent transfer device in accordance with the present invention is shown in FIGS. 1–4. Referring to FIG. 1, the transfer device includes a transfer member 10 having an array of reagent sampling pins 12. The transfer device further includes a reagent tray 14 having an array of reagent wells 16, as shown in FIG. 2. The array of pins 12 corresponds to the array of wells 16 so that the pins 12 can be simultaneously dipped into the corresponding wells 16 when the transfer member 10 is moved downward to a position proximate the reagent tray 14. The array of wells 16 contains at least about 100 wells with a density of at least about 100 wells per square centimeter. In a preferred embodiment, the wells 16 are arranged in a two-dimensional array of 32 wells by 32 wells for a total of 1,024 reagent wells 16. Each of the wells 16 has a very small width a which is no greater than about 300 microns. Alternatively, the wells 16 can be cylindrical with a diameter no greater than about 300 microns. Adjacent wells 16 in the array are spaced apart by a center-to-center distance b which is less than about 500 microns, and preferably about 350 microns. In this way, the array of wells 16 has a density of approximately 1,000 wells per square centimeter on the surface of the reagent tray 14. Similarly, the pins 12 on the surface of the transfer member 10 are arranged in a two-dimensional array of 32 pins by 32 pins for a total of 1,024 pins 12. Each of the pins 12 in the array has a diameter in the range of between about 30 microns and about 100 microns.

Figure 3:
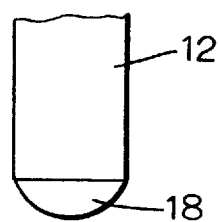
FIG. 3 is a partial side view of a pin according to the present invention with a reagent sample in the form of a fluid drop deposited thereon.

Reagent samples are deposited on the pins 12 when the pins 12 are dipped into the corresponding wells 16. Each of the wells 16 contains a supply of reagent, a portion of which is transferred by the pins 12 to a deposit surface 20 (see FIG. 2). FIG. 3 illustrates the end portion of a pin 12 with a reagent sample in the form of a fluid drop 18. Each of the pins 12 has an outer shape adapted to retain a reagent sample when the pin 12 is dipped into one of the wells 16. In a preferred embodiment, the outer shape of each of the pins 12 is cylindrical. The reagent in the wells 16 adheres to the outer surface of the pin 12, and the fluid drop 18 remains adhered to the pin 12 when the pin 12 is retracted from the well 16. When the transfer member 10 is moved into position proximate the deposit surface 20, the fluid drop 18 contacts and adheres to the deposit surface, thereby leaving the reagent sample on the deposit surface 20 when the pin 12 is retracted from the deposit surface.

Figure 4:
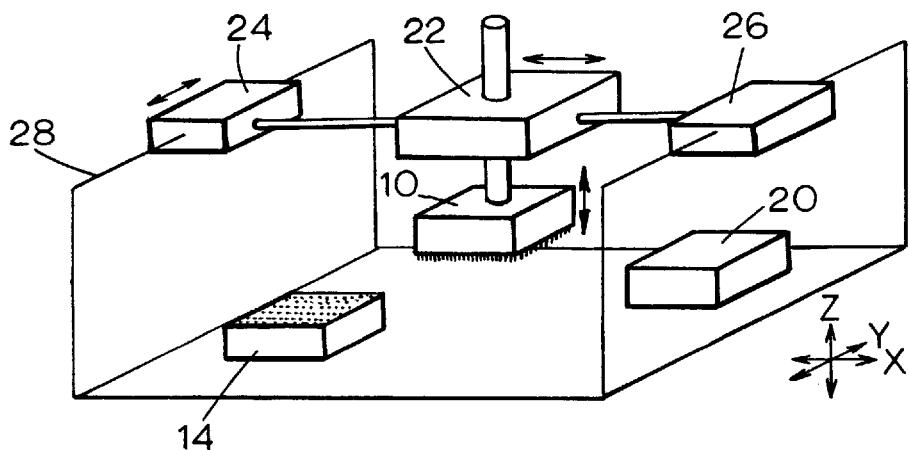
FIG. 4 is a schematic view of a system for moving a transfer member between a reagent tray and a deposit surface.

One arrangement of an automated system for moving the transfer member 10 between the reagent tray 14 and the deposit surface 20 is illustrated schematically in FIG. 4. The transfer member 10 is mounted to a carriage 22 which is positioned above the transfer member 10. The carriage 22 in turn is mounted between a first positioning member 24 and a second positioning member 26. The positioning members 24, 26 are mounted on opposite sides of a frame 28. The carriage 22 contains a drive mechanism which provides independent movement in the Z-direction of the transfer member 10. Additionally, the drive mechanism of the carriage 22 moves the carriage 22 and the transfer member 10 laterally between the positioning members 24, 26 in the X-direction. Finally, the positioning members 24, 26 and, correspondingly the transfer member 10 and the carriage 22, move back and forth in the Y-direction along the frame 28 under the influence of a drive mechanism in either or both of the positioning members 24, 26. In this way, the transfer member 10 is moved independently in the X-direction, the Y-direction and the Z-direction between the reagent tray 14 and the deposit surface 20.

To begin the process of transferring a plurality of reagent samples from the reagent tray 14 to the deposit surface 20, the transfer member 10 is positioned above the reagent tray 14. The drive mechanisms in the carriage 22 and the positioning members 24, 26 move the transfer member 10 in the X-direction and Y-direction, respectively, until the transfer member 10 is aligned above the reagent tray 14. Once positioned, the drive mechanism in the carriage 22 moves the transfer member 10 downwardly in the Z-direction to dip the pins 12 into the corresponding wells 16. The drive mechanism of the carriage 22 reverses to withdraw the transfer member 10 from the regent tray 14 with the reagent samples adhering to the pins 12. The drive mechanism in the carriage 22 and the positioning members 24, 26 reposition the transfer member 10 in the X-direction and Y-direction, respectively, until the transfer member 10 is positioned above the deposit surface 20. The drive mechanism in the carriage 22 moves the transfer member 10 downwardly until the reagent samples contact the deposit surface 20. The reagent samples adhere to the deposit surface 20 and remain on the deposit surface 20 when the drive mechanism of the carriage 22 is reversed, thereby moving the transfer member 10 upwardly in the Z-direction away from the deposit surface 20.

The particular arrangement for positioning the transfer member 10 described herein is illustrative only. Additionally, the arrangement may include mechanisms for moving the deposit surfaces 20 in the X-direction and the Y-direction into position to receive the reagent samples. Other automated mechanisms for moving the transfer member 10 and the deposit surface 20 will be obvious to those of ordinary skill in the art and are contemplated by the inventor having use in connection with the present invention.

Figure 5:
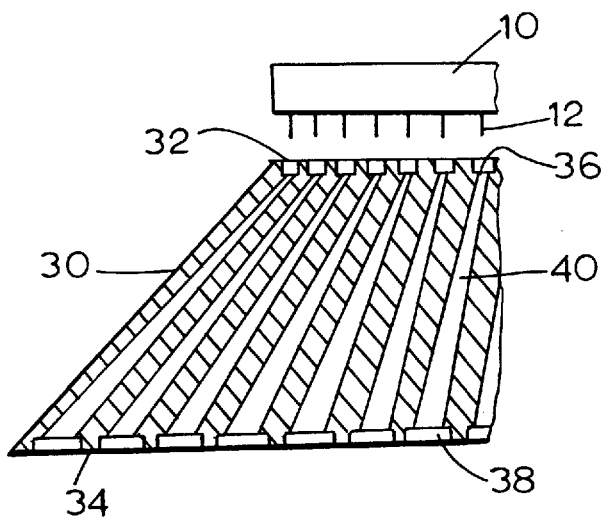
FIG. 5 is a partial side sectional view of an alternative embodiment of the reagent tray according to the present invention.

FIG. 5 is a partial side sectional view of an alternative embodiment of a reagent tray 30 in accordance with the present invention. The reagent tray 30 is formed generally in the shape of a pyramid with a top surface 32 having a smaller surface area than a bottom surface 34. In a preferred embodiment, the top surface 32 is about 1 centimeter by 1 centimeter and the bottom surface 34 is about 30 centimeters by 30 centimeters. The top surface 32 of the reagent tray 30 has an array of wells 36 formed thereon similar to the array of wells 16 previously illustrated and discussed in relation to FIG. 2. The bottom surface 34 has an array of coupling cavities 38 corresponding to the array of wells 36 on the top surface 32. The coupling cavities 38 have a larger diameter than the wells 36 to facilitate attachment of reagent supply lines (not shown) to the bottom surface 34. The larger diameter of the coupling cavities 38 necessitates the increased surface area of the bottom surface 34. Each well 36 is placed in fluid communication with the corresponding coupling cavity 38 by a channel 40 which connects the bottom of the well 36 to the top of the coupling cavity 38. Reagent from the reagent supply lines passes through the coupling cavities 38 and the channels 40 to the wells 36 to replenish the supply of reagent in the wells 36.

Figure 6:
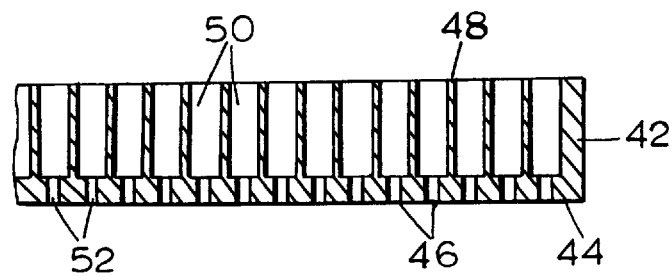
FIG. 6 is a partial side sectional view of an alternative embodiment of the transfer member according to the present invention.

Another alternative embodiment for a reagent transfer device according to the present invention is shown in FIGS. 6–9. In this embodiment, a transfer member 42 performs both functions of supplying the reagent for the reagent samples and transferring the reagent samples to a deposit surface. Referring to FIG. 6, the transfer member 42 has a bottom surface 44 with an array of orifices 46. The array of orifices 46 contains at least 100 orifices with a density of at least about 100 orifices per square centimeter of bottom surface area. A top surface 48 of the transfer member 42 has an array of reservoirs 50 which corresponds to the array of orifices in the bottom surface 44. Each reservoir 50 is placed in fluid communication with the corresponding orifice 46 by a channel 52 which connects the bottom of the reservoir 50 to the orifice 46. The transfer member 42 is mounted on a mechanism (not shown) for positioning the transfer member 42 proximate a deposit surface (not shown) to deposit a plurality of reagent samples thereon.

FIG. 7 is a bottom view of the transfer member 42 which shows the orifices 46 on its bottom surface 44. The orifices 46 are arranged in a two-dimensional array of 32 orifices by 32 orifices for a total of 1,024 orifices 46. Each of the orifices 46 has a very small diameter c which is no greater than about 100 microns. Adjacent orifices 46 in the array are spaced apart by a center-to-center distance d which is less than about 500 microns, and preferably about 350 microns. In this way, the array of orifices 46 has a density of approximately 1,000 orifices 46 per square centimeter on the bottom surface 44 of the transfer member 42.

Referring to FIG. 8, which is an enlarged view of a portion of the transfer member 42, reagent samples are formed on the bottom surface 44 of the transfer member 42 about each of the orifices 46. Reagent from the reservoir 50 passes through the channel 48 to the orifice 46. As reagent passes through the orifice 46 and adheres to the bottom surface 44 of the transfer member 42, a reagent sample is created in the form of a fluid drop 54. When the transfer member 42 is moved into position proximate the deposit surface (not shown), the fluid drop 54 contacts and adheres to the deposit surface, leaving the reagent sample on the deposit surface when the transfer member 42 is retracted from the deposit surface.

One arrangement for moving the transfer member 42 into contact with a plurality of deposit surfaces 56–68 is illustrated schematically in FIG. 9. The transfer member 42 is mounted to a carriage 70 above a rotating shelf 72. The carriage 70 includes a drive mechanism which moves the transfer member 42 upwardly and downwardly in the Z-direction. The deposit surfaces 56–68 are arranged on the shelf 72 so that the deposit surfaces 56–68 pass under the transfer member 42 as the shelf 72 rotates in the direction indicated by the arrows. The rotation of the shelf 72 is precisely controlled to stop when one of the deposit surfaces 56–68 is positioned beneath the transfer member 42.

The drive mechanism of the carriage 70 moves the transfer member 42 downwardly until the transfer member 42 is close enough to the deposit surface 56 for the fluid drops 54 to contact the deposit surface 56. After the fluid drops 54 contact the deposit surface 56, the transfer member 42 is retracted from the deposit surface 56, leaving the reagent samples deposited thereon. A new set of fluid drops 54 is formed on the bottom surface 44 of the transfer member 42 by passing additional reagent from the reservoirs 50 through the channels 48 to the orifices 46. In preparation for depositing reagent samples on the next deposit surface 58, the shelf 72 is rotated to position the deposit surface 58 under the transfer member 42. Once positioned, the transfer member 42 is lowered toward the deposit surface 58.

This arrangement for transferring a plurality of reagent samples from the transfer member 42 to the deposit surfaces 56–68 is illustrative only. Alternatively, an arrangement similar to that illustrated schematically in FIG. 4 may be used to move the transfer member in the X-direction, the Y-direction and the Z-direction in order to deposit reagent samples on the deposit surfaces 56–68. Additional mechanisms for positioning the transfer member 42 and the deposit surfaces 56–68 will be obvious to those of ordinary skill in the art and are contemplated by the inventor as having use in connection with the present invention.

While the present invention has been described with reference to the specific examples, which are intended to be illustrative only and not to be limiting of the invention, it will be apparent to those of ordinary skill in the art that changes, additions, and/or deletions may be made to the disclosed embodiment without departing from the spirit and scope of the invention.

What is claimed is:

1. A reagent transfer device for transferring a plurality of reagent samples from one location to another location having a deposit surface, comprising:
   a reagent tray comprising:
      a top surface with a top surface area and a plurality of wells arranged in a two-dimensional array of at least 30 wells by at least 30 wells, the wells having a diameter no greater than about 300 microns and being spaced apart by a center-to-center distance measured from the center of one well to the center of an adjacent well of less than about 500 microns; and a bottom surface having a bottom surface area larger than the top surface area, a plurality of coupling cavities, and a plurality of channels, each of the channels connecting one of the wells to a corresponding one of the coupling cavities so that the one well and the one corresponding coupling cavity are in fluid communication so as to allow replenishment of the one well by providing reagent to the one well through the one corresponding coupling cavity and the channel;

a transfer member having a transfer surface with a two-dimensional array of pins extending therefrom, each of the pins positioned to correspond to one of the wells so that when the transfer member is moved in the Z-direction the pins are simultaneously dipped into the corresponding wells; and means for moving the transfer member between a first position in which reagent from the wells is deposited on the pins and a second position in which reagent on the pins is deposited on the deposit surface, the means for moving comprising:
  means for moving the transfer member in the X-direction;
  means for moving the transfer member in the Y-direction; and
  means for moving the transfer member in the Z-direction.

2. A reagent transfer device according to claim 1, wherein each of the pins has a diameter in the range of between about 30 microns and about 100 microns.

3. A reagent transfer device according to claim 1, wherein each of the pins has an outer shape adapted to retain a sample of one of the reagents when the pin is dipped into the corresponding one of the wells.

4. A reagent transfer device for transferring a plurality of reagent samples from one location to another location having a deposit surface, comprising:

a reagent tray having a top surface with a top surface area and at least about 100 wells in the ratio of at least about 100 wells per square centimeter of top surface area, a bottom surface having a bottom surface area larger than the top surface area and a plurality of coupling cavities, and a plurality of channels, each of the channels connecting one of the given wells to a corresponding one of the coupling cavities so that the one well and the one corresponding coupling cavity are in fluid communication so as to allow replenishment of the one well by providing reagent to the one well through the corresponding coupling cavity and the channel;

a transfer member having a transfer surface with a plurality of pins extending therefrom, each of the pins positioned to correspond to one of the wells so that when the transfer member is moved in the Z-direction the pins are simultaneously dipped into the corresponding wells; and means for moving the transfer member between a first position in which reagent from the wells is deposited onto the corresponding pins and a second position in which reagent on the pins is deposited on the deposit surface, the means for moving adapted to move the transfer member in the X-direction, the Y-direction and the Z-direction.

5. A method for transferring a plurality of reagent samples from a reagent tray via a transfer member to a deposit surface, the reagent tray having a top surface with a top surface area and at least about 100 wells in the ratio of at least about 100 wells per square centimeter of top surface area, and the transfer member having a transfer surface with a plurality of pins extending therefrom, each of the pins position to correspond to one of the wells so that when the transfer member is moved in the Z-direction the pins are simultaneously dipped into the corresponding wells, and wherein the reagent tray has a bottom surface having a bottom surface area, a plurality of coupling cavities, and a plurality of channels, each of the channels connecting one of the wells to a corresponding one of the coupling cavities so that the one well and the one corresponding coupling cavity are in fluid communication, the method comprising the steps of:

dipping the pins into the corresponding wells so that a reagent sample is deposited on each of the pins by adhesion to the outer surface of the pins;

moving the transfer member to a position proximate the deposit surface;

contacting the deposit surface with the reagent samples, whereby the reagent samples are deposited on the deposit surface by adhesion to the deposit surface; and replenishing the reagent in the wells by providing reagent to the wells through the one corresponding coupling cavities and the channels.

\* \* \* \* \*